US011471430B2

(12) United States Patent
Futerman et al.

(10) Patent No.: US 11,471,430 B2
(45) Date of Patent: Oct. 18, 2022

(54) SPHINGOSINE ANALOGS AND USE THEREOF AGAINST BACTERIAL LUNG INFECTIONS (71) Applicants: Yeda Research and Development Co. Ltd., Rehovot (IL); University of Duisburg-Essen, Essen (DE)

(72) Inventors: Anthony H. Futerman, Rehovot (IL); Tammar Joseph, Rehovot (IL); Walter A. Shaw, Rehovot (IL); Stephen W. Burgess, Rehovot (IL); Shengrong Li, Rehovot (IL)

(73) Assignees: Yeda Research and Development Co. Ltd., Rehovot (IL); University of Duisburg-Essen, Essen (DE)

( * ) Notice: Subject to any disclaimer, the term of this patent is extended or adjusted under 35 U.S.C. 154(b) by 0 days.

(21) Appl. No.: 17/261,255

(22) PCT Filed: Jul. 17, 2019

(86) PCT No.: PCT/IL2019/050806
§ 371 (c)(1),
(2) Date: Jan. 19, 2021

(87) PCT Pub. No.: WO2020/016894
PCT Pub. Date: Jan. 23, 2020

(65) Prior Publication Data
US 2021/0275473 A1  Sep. 9, 2021

(30) Foreign Application Priority Data

Jul. 19, 2018  (IL) .......................................... 260690

(51) Int. Cl.
| *A61K 31/167* | (2006.01) |
| *A61K 31/133* | (2006.01) |
| *A61K 31/164* | (2006.01) |

(52) U.S. Cl.
CPC .......... *A61K 31/167* (2013.01); *A61K 31/133* (2013.01); *A61K 31/164* (2013.01)

(58) Field of Classification Search
CPC .. A61K 31/133; A61K 31/135; A61K 31/164; A61K 31/167; A61P 31/04; Y02A 50/30
See application file for complete search history.

(56) References Cited

U.S. PATENT DOCUMENTS

| 6,147,118 | A | 11/2000 | Lambers et al. | |
| 6,881,546 | B2 | 4/2005 | Sabbadini | |
| 2005/0036951 | A1 | 2/2005 | Henderson | |
| 2005/0209219 | A1 | 9/2005 | Gulbins | |
| 2010/0285139 | A1 | 11/2010 | Gulbins | |
| 2015/0258043 | A1* | 9/2015 | Futerman | A61K 31/133 |
| | | | | 514/25 |

FOREIGN PATENT DOCUMENTS

| EP | 1287815 | 3/2003 |
| WO | WO 99/41266 | 8/1999 |
| WO | WO 03/045365 | 6/2003 |
| WO | WO 2007/003904 | 1/2007 |
| WO | WO 2008/006007 | 1/2008 |
| WO | WO 2008/124210 | 10/2008 |
| WO | WO 2009/011007 | 1/2009 |
| WO | WO 2009/141627 | 11/2009 |
| WO | WO 2010/081026 | 7/2010 |
| WO | WO 2011/133584 | 10/2011 |
| WO | WO 2014/061016 | 4/2014 |
| WO | WO 2016172380 | * 10/2016 |
| WO | WO 2020/016894 | 1/2020 |

OTHER PUBLICATIONS

Fighting the Impact of Antibiotic-Resistant Bacteria, FDA Consumer Health Information, 2013 (Year: 2013).*
Banker et al., Prodrugs, Modern Pharmaceutics, Third Edition and Expanded, pp. 451 and 596 (1996) (Year: 1996).*
Wolff, Burger's Medicinal Chemistry and Drug Discovery, 5th Edition, vol. I Principles and Practice, pp. 975-977, 1995 (Year: 1995 ).*
Bundgaard (Design of Prodrugs, 1985, chapter 1) (Year: 1985).*
Silverman (Prodrugs and Drug Delivery Systems, The Organic Chemistry of Drug Design and Drug Action, pp. 352-399, 1992) (Year: 1992).*
Communication Pursuant to Rule 164(1) EPC and Supplementary Partial European Search Report dated Mar. 7, 2016 From the European Patent Office Re. Application No. 13846807.9.
International Preliminary Report on Patentability dated Jan. 28, 2021 From the International Bureau of WIPO Re. Application No. PCT/IL2019/050806. (7 Pages).
International Preliminary Report on Patentability dated Apr. 30, 2015 From the International Bureau of WIPO Re. Application No. PCT/IL2013/050831.
International Search Report and the Written Opinion dated Jan. 16, 2014 From the International Searching Authority Re. Application No. PCT/IL2013/050831.
International Search Report and the Written Opinion dated Oct. 23, 2019 From the International Searching Authority Re. Application No. PCT/IL2019/050806. (14 Pages).
Office Action dated Feb. 21, 2019 From the Israel Patent Office Re. Application No. 260690. (6 Pages).
Official Action dated Sep. 6, 2016 From the US Patent and Trademark Office Re. U.S. Appl. No. 14/435,848.
Official Action dated Sep. 8, 2017 From the US Patent and Trademark Office Re. U.S. Appl. No. 14/435,848. (8 pages).
Official Action dated Mar. 15, 2018 From the US Patent and Trademark Office Re. U.S. Appl. No. 14/435,848. (10 pages).
Official Action dated Apr. 19, 2017 From the US Patent and Trademark Office Re. U.S. Appl. No. 14/435,848. (10 pages).
Restriction Official Action dated Jun. 3, 2016 From the US Patent and Trademark Office Re. U.S. Appl. No. 14/435,848.

(Continued)

*Primary Examiner* — Umamaheswari Ramachandran (57) ABSTRACT

Provided herein is a group of sphingosine analogs, useful in the treatment of bacterial infections in mucosal surfaces such as lungs, caused by pathogenic bacteria which are typical to disorders and diseases such as CF and COPD.

9 Claims, 4 Drawing Sheets

(56) References Cited

OTHER PUBLICATIONS

Supplementary European Search Report and the European Search Opinion dated May 9, 2016 From the European Patent Office Re. Application No. 13846807.9.

Bar-Haim et al. "Interrelationship Between Dendritic Cell Trafficking and Francisella Tularensis Dissemination Following Airway Infection", PLoS Pathogens, XP002757029, 4(11): e1000211-1-e1000211-16, Nov. 21, 2008.

Becam et al. "Antibacterial Activity of Ceramide and Ceramide Analogs Against Pathogenic Neisseria", Scientific Reports, 7: 17627-1-17627-12, Published Online Dec. 15, 2017.

Bibel et al. "Antimicrobial Activity of Sphingosines", Journal of Investigative Dermatology, 98(3):269-273, Mar. 1992.

Fischer et al. "Antibacterial Activity of Sphingoid Bases and Fatty Acids Against Gram-Positive and Gram-Negative Bacteria", Antimicrobial Agents and Chemotherapy, XP055253270, 56(3): 1157-1161, Published Online Dec. 12, 2011.

Idzko et al. "Local Application of FTY720 to the Lung Abrogates Experimental Asthma by Altering Dendritic Cell Function", The Journal of Clinical Investigation, XP002757030, 116(11): 2935-2944, Nov. 1, 2006. Abstract.

Pewzner-Jung et al. "Sphingoid Long Chain Bases Prevent Lung Infection bv Pseudonomas Aeruginosa", EMBO Molecular Medicine, 6(9): 1205-1214, Published Online Aug. 1, 2014.

Santel et al. "A Novel SiRNA-Lipoplex Technology for RNA Interference in the Mouse Vascular Endothelium", Gene Therapy, XP002459352, 13(16): 1222-1234, Published Online Apr. 20, 2006.

Seitz et al. "Ceramide and Sphingosine in Pulmonary Infections", Biological Chemistry, 396(6-7): 611-620, Jan. 14, 2015.

Wenderska et al. "Palmitoyl-DL-Carnitine Is a Multitarget Inhibitor of Pseudomonas Aeruginosa Biofilm Development", ChemBioChem, 12(18): 2759-2766, Dec. 16, 2011.

Yang et al. "The Role of Sphingolipids in Respiratory Disease", Therapeutic Advances in Respiratory Disease, XP009163905, 5(5): 325-344, Oct. 1, 2011.

\* cited by examiner

SPHINGOSINE ANALOGS AND USE THEREOF AGAINST BACTERIAL LUNG INFECTIONS

RELATED APPLICATIONS

This application is a National Phase of PCT Patent Application No. PCT/IL2019/050806 having International filing date of Jul. 17, 2019, which claims the benefit of priority of Israel Patent Application No. 260690 filed on Jul. 19, 2018, The contents of the above applications are all incorporated by reference as if fully set forth herein in their entirety.

FIELD AND BACKGROUND OF THE INVENTION

The present invention, in some embodiments thereof, relates to medicinal agents and uses thereof, and more particularly, but not exclusively, to a family of sphingosine analogs and uses thereof in treating bacterial lung infections.

Cystic fibrosis (CF) patients, and patients with chronic obstructive pulmonary disease (COPD), are particularly susceptible to *Pseudomonas aeruginosa* infection, with approximately 80% of CF patients suffering from chronic *P. aeruginosa* pneumonia by 25 years of age, and one-third of patients with COPD hosting the bacteria. However, the increasing rate of *P. aeruginosa* resistance to many antibiotics necessitates the development of alternative therapies, which might also be beneficial in preventing *P. aeruginosa* infection in patients with trauma, burn wounds, sepsis, or in patients requiring ventilation.

Previous studies have demonstrated that various natural lipids and lyso-lipids act as bactericidal agents in skin. Certain fatty acids and sphingoid bases found at mucosal surfaces are known to have antibacterial activity and are thought to play a more direct role in innate immunity against bacterial infections. Among these is the sphingoid long chain base (LCB), sphingosine (SPH), which protects human skin from bacterial colonization. SPH is generated by hydrolysis of ceramide via acid ceramidase (AC). We now demonstrate that tracheal and bronchial epithelial SPH levels play a vital role in preventing normal individuals from *P. aeruginosa* lung infection. SPH levels are significantly reduced in tracheal and bronchial epithelia of CF patients and of CF mice, due to reduced AC activity, and normalization of SPH levels reverses susceptibility to *P. aeruginosa*.

Several studies indicate the importance of acid sphingomyelinase and its product ceramide in infection of mammalian cells with a variety of pathogens including *P. aeurginosa*, *Staphylococcus aureus* (*S. aureus*), *Neisseria gonorrohoea*, *Mycobacteria*, *Salmonella typhi*, *Listeria monocytogenes* and *E. coli*. Further studies revealed that ceramide levels are increased in airway epithelial cells of patients with CF and that ceramide is an important mediator in pulmonary infection of CF patients with *P. aeruginosa*. However, it is unknown whether other sphingolipids, such as sphingosine, which is generated from ceramide by ceramidases, play a role in pulmonary infection, particularly in individuals with recurrent bacterial infections such as in CF.

International Patent Application No. WO 2008/006007 provides treatment of CF and *P. aeruginosa* infections by administering a therapeutic amount of one or more agents that inhibit de novo sphingolipid synthesis or recycling pathways.

U.S. Patent Application No. 2005/0209219, to one of the inventors of the present invention, relates to the use of inhibitors of acid sphingomyelinase and/or inhibitors of products of the reaction catalyzed by said enzyme, for the prophylaxis and/or treatment of infectious diseases and/or diseases which are influenced by infections during the course thereof. Preferably, neutralizing antibodies and/or anti-depressants, especially tricyclic and/or tetracyclic and depressants, are used as inhibitors.

Wenderska, I. B. et al. (*ChemBioChem*, 2011, 12, pp. 2759-2766) discloses small molecules inhibitors of *P. aeruginosa* biofirm formation.

Bibel, D. J. et al. (*J Invest Dermatol.* 1992, 98(3), pp. 269-73) describes the antimicrobial activity of sphingosines against *Staphylococcus aureus* and other bacteria.

Becam, J. et al. (*Sci Rep.*, 2017, 7(1), p. 17627) reports antibacterial activity of ceramide and ceramide analogs against pathogenic *Neisseria*.

U.S. Patent Application No. 2010/0285139 to one of the inventors of the present invention, relates to pharmaceutical composition for prophylaxis and/or treatment of infections and/or infectious diseases occurring in CF includes at least one antidepressant; at least one dispersant; and at least one pharmaceutically tolerable carrier material.

Pewzner-Jung Y. et al. (*EMBO Mol Med.*, 2014, 6(9), pp. 1205-14) and U.S. Patent Application No. 2015/0258043, to one of the inventors of the present invention, relates to methods of preventing or treating *P. aeruginosa* infections by administering sphingoid long chain bases (LCB), in the treatment of lung diseases or disorders such as CF and COPD.

SUMMARY OF THE INVENTION

According to an aspect of some embodiments of the present invention there is provided a sphingosine analog, selected individually from the group consisting of:

(2S,3S)-2-(dimethylamino)octadecane-1,3-diol [791577]

(2S,3S)-1-amino-2-(dimethylamino)octadecane-3-ol [791578]

(2S,3R)-$N^2$,$N^2$-dimethyloctadecane-1,2,3-triamine [791579]

(2S,3S)-$N^2$,$N^2$-dimethyloctadecane-1,2,3-triamine [791580]

(E)-2-aminohexadec-5-ene-1,2-diol [791581]

(E)-hexadec-5-ene,1,2,2-triamine [791582]

(2R,3R)-1,2-diaminooctadecan-3-ol [791597]

(2R,3S)-octadecan-1,2,3-triamine [791598]

(2R,3R,Z)-2-aminohenicos-12-ene-1,3-diol [791601]

(2S,3S,12Z,15Z)-2-aminohenicosa-12,15-diene-1,3-diol [791602]

(R)-2,3-diamino-N-tetradecylpropanamide [791993]

-continued

(S)-2,3-diamino-N-tetradecylpropanamide [791994]

(S)-2,3-diamino-N-(4-dodecylphenyl)propanamide [791995]

(S)-2,3-diamino-N-(4-dodecylphenyl)propanamide [791996]

(S)-2,3-diamino-N-(4-dodecylphenyl)propanamide [791996]

2,3-diamino-N-(4-tetradecylphenyl)propanamide [792205]

(S)-2,3-diamino-N-(4-hexadecylphenyl)propanamide [792206]

2,3-diamino-N-hexadecylpropanamide [792208]

2,3-diamino-N-octadecylpropanamide [792209]

3-amino-N-(4-dodecylphenyl)-2-hydroxypropanamide [792211]

-continued (S)-2,4-diamino-N-(4-dodecylphenyl)butanamide [792212]

and any prodrug, solvate, hydrate and/or pharmaceutically acceptable salt thereof.

According to an aspect of some embodiments of the present invention there is provided a pharmaceutical composition comprising, as an active ingredient, one or more of the sphingosine analog presented herein.

According to an aspect of some embodiments of the present invention there is provided a use of the sphingosine analog presented herein for the preparation of a medicament.

In some embodiments of the invention, the sphingosine analog in the pharmaceutical composition, or the sphingosine analog used for the preparation of a medicament, is 791577.

In some embodiments of the invention, the sphingosine analog in the pharmaceutical composition, or the sphingosine analog used for the preparation of a medicament, is 791578.

In some embodiments of the invention, the sphingosine analog in the pharmaceutical composition, or the sphingosine analog used for the preparation of a medicament, is 791579.

In some embodiments of the invention, the sphingosine analog in the pharmaceutical composition, or the sphingosine analog used for the preparation of a medicament, is 791580.

In some embodiments of the invention, the sphingosine analog in the pharmaceutical composition, or the sphingosine analog used for the preparation of a medicament, is 791581.

In some embodiments of the invention, the sphingosine analog in the pharmaceutical composition, or the sphingosine analog used for the preparation of a medicament, is 791582.

In some embodiments of the invention, the sphingosine analog in the pharmaceutical composition, or the sphingosine analog used for the preparation of a medicament, is 791597.

In some embodiments of the invention, the sphingosine analog in the pharmaceutical composition, or the sphingosine analog used for the preparation of a medicament, is 791598.

In some embodiments of the invention, the sphingosine analog in the pharmaceutical composition, or the sphingosine analog used for the preparation of a medicament, is 791601.

In some embodiments of the invention, the sphingosine analog in the pharmaceutical composition, or the sphingosine analog used for the preparation of a medicament, is 791602.

In some embodiments of the invention, the sphingosine analog in the pharmaceutical composition, or the sphingosine analog used for the preparation of a medicament, is 791993.

In some embodiments of the invention, the sphingosine analog in the pharmaceutical composition, or the sphingosine analog used for the preparation of a medicament, is 791994.

In some embodiments of the invention, the sphingosine analog in the pharmaceutical composition, or the sphingosine analog used for the preparation of a medicament, is 791995.

In some embodiments of the invention, the sphingosine analog in the pharmaceutical composition, or the sphingosine analog used for the preparation of a medicament, is 791996.

In some embodiments of the invention, the sphingosine analog in the pharmaceutical composition, or the sphingosine analog used for the preparation of a medicament, is 792205.

In some embodiments of the invention, the sphingosine analog in the pharmaceutical composition, or the sphingosine analog used for the preparation of a medicament, is 792206.

In some embodiments of the invention, the sphingosine analog in the pharmaceutical composition, or the sphingosine analog used for the preparation of a medicament, is 792208.

In some embodiments of the invention, the sphingosine analog in the pharmaceutical composition, or the sphingosine analog used for the preparation of a medicament, is 792209.

In some embodiments of the invention, the sphingosine analog in the pharmaceutical composition, or the sphingosine analog used for the preparation of a medicament, is 792211.

In some embodiments of the invention, the sphingosine analog in the pharmaceutical composition, or the sphingosine analog used for the preparation of a medicament, is 792212.

In some embodiments of the invention, the pharmaceutical composition or the medicament is identified for use in preventing or treating a bacterial infection in a subject.

In some embodiments of the invention, the bacteria is a gram-positive bacteria or a gram-negative bacteria.

In some embodiments of the invention, the bacterial infection is caused by a pathogenic species selected from the group consisting of *Pseudomonas* species, *Staphylococcus* species, *Acinetobacter* species, *Burkholderia* species, *Neisseria* species *Salmonella* species, *Listeria* species and/or *Mycobacteria* species.

In some embodiments of the invention, the bacterial infection is caused by *Pseudomonas aeruginosa*.

In some embodiments of the invention, the bacterial infection is a pulmonary bacterial infection.

In some embodiments of the invention, the bacterial infection is in a subject having a lung disorder or disease.

In some embodiments of the invention, the lung disorder or disease is selected from the group consisting of cystic fibrosis (CF), chronic obstructive pulmonary disease (COPD) and pneumonia.

According to an aspect of some embodiments of the present invention there is provided a use of the sphingosine analog presented herein for preventing or treating a bacterial infection in a subject in need thereof.

According to an aspect of some embodiments of the present invention there is provided a method for preventing or treating a bacterial infection in a subject in need thereof, comprising the step of administering to the subject a therapeutically effective amount of the sphingosine analog presented herein.

In some embodiments of the invention, the treatment is effected by inhalation.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SOME SPECIFIC EMBODIMENTS OF THE INVENTION

The present invention, in some embodiments thereof, relates to medicinal agents and uses thereof, and more particularly, but not exclusively, to a family of sphingosine analogs and uses thereof in treating bacterial lung infections.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As mentioned hereinabove, *Pseudomonas aeruginosa* is the leading respiratory pathogen and eventual cause of death for patients with Cystic Fibrosis (CF). The molecular mechanisms that lead to increased susceptibility of CF patients to *P. aeruginosa* are unknown. In previous studies by the present inventor, it has been demonstrated that *P. aeruginosa* infections in CF can be prevented by treatment with FTY720 (fingolimod) or with sphingosine (SPH), whereas FTY720 is a sphingosine analog. When CF mice were injected with either sphingosine, or with FTY720, immediately prior to infection, or an hour after infection, the infection was completely blocked. In addition, it has been demonstrated in ten new SPH analogs in vitro and in vivo.

Novel Sphingosine Analogs:

While searching for more efficacious sphingosine analogs, the present inventors have developed, synthesized and tested several novel sphingosine analogs, set forth in Table 1 below, referred to herein as "the sphingosine analogs".

Thus, according to an aspect of embodiments of the present invention, there is provided a sphingosine analog, individually selected from the compounds set forth in Table 1 below, and any prodrugs, solvates, hydrates and/or pharmaceutically acceptable salts thereof.

The term "prodrug" refers to an agent, which is converted into the active polymer (the active parent drug) in vivo. Prodrugs are typically useful for facilitating the administration of the parent drug. They may, for instance, be bioavailable by oral administration whereas the parent drug is not. A prodrug may also have improved solubility as compared with the parent drug in pharmaceutical compositions. Prodrugs are also often used to achieve a sustained release of the active compound in vivo. An example, without limitation, of a prodrug would be a compound of the present invention, having one or more carboxylic acid moieties, which is administered as an ester (the "prodrug"). Such a prodrug is hydrolyzed in vivo, to thereby provide the free compound (the parent drug). The selected ester may affect both the solubility characteristics and the hydrolysis rate of the prodrug.

The term "solvate" refers to a complex of variable stoichiometry (e.g., di-, tri-, tetra-, penta-, hexa-, and so on), which is formed by a solute (the polymer as described herein) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

The phrase "pharmaceutically acceptable salt" refers to a charged species of the parent polymer and its counter ion, which is typically used to modify the solubility characteristics of the parent compound and/or to reduce any significant irritation to an organism by the parent polymer, while not abrogating the biological activity and properties of the administered polymer. An example, without limitation, of a pharmaceutically acceptable salt would be a carboxylate anion and a cation such as, but not limited to, ammonium, sodium, potassium and the like.

It is noted that herein and throughout, referring to the sphingosine analogs presented herein is to be understood as referring to any individual one, any combination of two, three or more of the sphingosine analogs presented herein. Each possibility represents a separate embodiment of the present invention. Correspondingly, any aspect pertaining to any one of the compounds presented herein (see Table 1 hereinbelow), and any embodiment of the invention which corresponds to a particular compound, can be excluded from the scope of the present invention without lessening the validity and/or generality of the invention as a whole.

Uses of the Sphingosine Analogs:

As contemplated herein, the present invention is based on the finding that the sphingosine analogs presented herein are active as antibacterial agents, especially against bacteria that thrive in mucous membranes, and microbial pathogens that are associated with lung infections (e.g., without limitation, in COPD or CF patients).

Thus, in one, the present invention relates to a method for preventing or treating a bacterial infection in a subject in need thereof comprising administering to the subject a therapeutically effective amount of a pharmaceutical composition comprising the sphingosine analogs presented herein and a pharmaceutically acceptable carrier, thereby preventing or treating a bacterial infection. When the bacterial infection is associated with a lung disorder, disease or infection, the sphingosine analogs presented herein may also be administered by inhalation. Other examples of routes of administration of the sphingosine analogs presented herein include oral or parenteral, e.g., intravenous, intradermal, transdermal (topical), transmucosal, and rectal administration, whereas each possibility represents a separate embodiment of the present invention.

In another aspect the present invention relates to a pharmaceutical composition comprising as an active ingredient the sphingosine analogs presented herein and a pharmaceutically acceptable carrier, for use in preventing or treating a bacterial infection, wherein the pharmaceutical composition is formulated for inhalation. When the bacterial infection is associated with a lung disorder, disease or infection, the pharmaceutical composition is formulated for administration from a suitable administration device, such as a metered-dose inhaler, a dry-powder inhaler, a reliever inhaler, and/or a slow mist inhaler/nebulizer. Each possibility represents a separate embodiment of the present invention.

In another aspect, the present invention relates to the use of the sphingosine analogs presented herein for the manufacture of a medicament beneficial for the prevention or treatment of a bacterial infection, wherein the medicament is formulated for inhalation. Other examples of routes of administration of the medicament include oral or parenteral, e.g., intravenous, intradermal, transdermal (topical), transmucosal, and rectal administration, whereas each possibility represents a separate embodiment of the present invention.

Underlying disease conditions can predispose a subject to acute and/or chronic bacterial infections. As used herein a "disease condition" refers to a pathological disease or condition of any kind or origin, which a subject harbors. Accordingly, disease conditions include the subject matter identified by the following diseases and/or terms including, but not limited to, e.g., a respiratory disease, lung disease, Cystic Fibrosis ("CF"), chronic obstructive pulmonary disease ("COPD"), emphysema, asthma, pulmonary fibrosis, chronic bronchitis, pneumonia, pulmonary hypertension, lung cancer, sarcoidosis, necrotizing pneumonia, asbestosis, aspergilloma, aspergillosis, acute invasive atelectasis, eosinophilic pneumonia, pleural effusion, pneumoconiosis, pneumocystosis, pneumothorax, pulmonary actinomycosis, pulmonary alveolar proteinosis, pulmonary anthracis, pulmonary arteriovenous malformation, pulmonary edema, pulmonary embolus, pulmonary histiocytosis X (eosinophilic granuloma), pulmonary nocardiosis, pulmonary tuberculosis, pulmonary veno-occlusive disease and/or rheumatoid lung disease. Such diseases typically manifest an increased susceptibility of a subject for bacterial infection, i.e., compared to subjects not afflicted with a disease condition. For example, subjects suffering from CF or COPD, may possess a high susceptibility for acquiring acute and/or chronic bacterial infections.

Examples of bacterial strain that can be treated by the compositions of the invention are all Gram-negative and Gram-positive bacteria and in particular gram negative and gram positive bacteria. The compounds of the present invention are effective against a wide variety of Gram-positive and Gram-negative bacteria, for example *Staphylococcus* species (e.g., *Staphylococcus aureus*), *Acinetobacter* species (e.g., *baumanii Acinetobacter*), *Pseudomonas* species (e.g., *Pseudomonas aeruginosa*), *Burkholderia* species, and *Mycobacteria* species (typical and atypical), and others. In some currently preferred embodiments, the bacterial infection is a *Pseudomonas* infection. In other current preferred embodiments, the *Pseudomonas* infection is a *Pseudomonas aeruginosa* infection.

Additional bacterial strains treatable by the sphingosine analogs presented herein, according to some embodiments of the present invention, include, but are not limited to *Acinetobacter baumanii, Actinobacillus* species, *Actinomycetes, Actinomyces* species (such as *Actinomyces israelii* and *Actinomyces naeslundii*), *Aeromonas* species (such as *Aeromonas hydrophila, Aeromonas veronii biovar sobria (Aeromonas sobria)*, and *Aeromonas caviae*), *Anaplasma phagocytophilum, Alcaligenes xylosoxidans, Acinetobacter baumanii, Actinobacillus actinomycetemcomitans, Bacillus* species (such as *Bacillus anthracis, Bacillus cereus, Bacillus subtilis, Bacillus thuringiensis*, and *Bacillus stearothermophilus*), *Bacteroides* species (such as *Bacteroides fragilis*), *Bartonella* species (such as *Bartonella bacilliformis* and *Bartonella henselae, Bifidobacterium* species, *Bordetella* species (such as *Bordetella pertussis, Bordetella parapertussis*, and *Bordetella bronchiseptica*), *Borrelia* species (such as *Borrelia recurrentis*, and *Borrelia burgdorferi*), *Brucella* species (such as *Brucella abortus, Brucella canis, Brucella melintensis* and *Brucella suis*), *Burkholderia* species (such as *Burkholderia pseudomallei* and *Burkholderia cepacia*), *Campylobacter* species (such as *Campylobacter jejuni, Campylobacter coli, Campylobacter lari* and *Campylobacter fetus*), *Capnocytophaga* species, *Cardiobacterium hominis, Chlamydia trachomatis, Chlamydophila Pneumococcus* species, *pneumoniae, Chlamydophila psittaci, Citrobacter* species *Coxiella burnetii, Corynebacterium* species (such as, *Corynebacterium diphtheriae, Corynebacterium jeikeum Corynebacterium*, and *Corynebacterium dipththeriae*), *Clostridium* species (such as *Clostridium perfringens, Clostridium difficile, Clostridium botulinum* and *Clostridium tetani*), *Eikenella corrodens, Enterobacter* species (such as *Enterobacter aerogenes, Enterobacter agglomerans, Enterobacter cloacae* and *Escherichia coli*, including opportunistic *Escherichia coli*, such as enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* species (such as *Enterococcus faecalis* and *Enterococcus faecium*) *Ehrlichia* species (such as *Ehrlichia chafeensia* and *Ehrlichia canis*), *Erysipelothrix rhusiopathiae, Eubacterium* species, *Francisella tularensis, Fusobacterium nucleatum, Gardnerella vaginalis, Gemella morbillorum, Haemophilus* species (such as *Haemophilus influenzae*, e.g., type B or non-typable, *Haemophilus ducreyi, Haemophilus aegyptius, Haemophilus parainfluenzae, Haemophilus haemolyticus* and *Haemophilus parahaemolyticus, Helicobacter* species (such as *Helicobacter pylori, Helicobacter cinaedi* and *Helicobacter fennelliae*), *Kingella kingii, Klebsiella* species (such as *Klebsiella pneumoniae, Klebsiella granulomatis* and *Klebsiella oxytoca*), *Lactobacillus* species, *Listeria monocytogenes, Leptospira interrogans, Legionella pneumophila, Leptospira interrogans, Peptostreptococcus* species, *Moraxella catarrhalis, Morganella* species, *Mobiluncus* species, *Micrococcus* species, *Mycobacterium* species (such as *Mycobacterium leprae, Mycobacterium tuberculosis, Mycobacterium intracellulare, Mycobacterium avium, Mycobacterium bovis*, and *Mycobacterium marinum*), *Mycoplasm* species (such as *Mycoplasma pneumoniae, Mycoplasma hominis*, and *Mycoplasma genitalium*), *Nocardia* species (such as *Nocardia asteroides, Nocardia cyriacigeorgica* and *Nocardia brasiliensis*), *Neisseria* species (such as *Neisseria gonorrhoeae* and *Neisseria meningitidis*), *Pasteurella multocida, Plesiomonas shigelloides. Prevotella* species, *Porphyromonas* species, *Prevotella melaninogenica, Proteus* species (such as *Proteus vulgaris* and *Proteus mirabilis*), *Providencia* species (such as *Providencia*

*alcalifaciens*, *Providencia rettgeri* and *Providencia stuartii*), *Pseudomonas aeruginosa*, *Propionibacterium acnes*, *Rhodococcus equi*, *Rickettsia* species (such as *Rickettsia rickettsii*, *Rickettsia akari* and *Rickettsia prowazekii*, *Orientia tsutsugamushi* (formerly: *Rickettsia tsutsugamushi*) and *Rickettsia typhi*), *Rhodococcus* species, *Serratia marcescens*, *Stenotrophomonas maltophilia*, *Salmonella* species (such as *Salmonella enterica*, *Salmonella typhi*, *Salmonella paratyphi*, *Salmonella enteritidis*, *Salmonella cholerasuis* and *Salmonella typhimurium*), *Serratia* species (such as *Serratia marcesans* and *Serratia liquifaciens*), *Shigella* species (such as *Shigella dysenteriae*, *Shigella flexneri*, *Shigella boydii* and *Shigella sonnei*), *Staphylococcus* species (such as *Staphylococcus aureus*, *Staphylococcus epidermidis*, *Staphylococcus hemolyticus*, *Staphylococcus saprophyticus*), *Streptococcus* species (such as *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae*, *Streptococcus mutans*, *Streptococcus pyogenes*, Group A streptococci, *Streptococcus pyogenes*, Group B streptococci, *Streptococcus agalactiae*, Group C streptococci, *Streptococcus anginosus*, *Streptococcus equismilis*, Group D streptococci, *Streptococcus bovis*, Group F streptococci, and *Streptococcus anginosus* Group G streptococci), *Spirillum minus*, *Streptobacillus moniliformi*, *Treponema* species (such as *Treponema carateum*, *Treponema petenue*, *Treponema pallidum* and *Treponema endemicum*, *Tropheryma whippelii*, *Ureaplasma urealyticum*, *Veillonella* species, *Vibrio* species (such as *Vibrio cholerae*, *Vibrio parahemolyticus*, *Vibrio vulnificus*, *Vibrio parahaemolyticus*, *Vibrio vulnificus*, *Vibrio alginolyticus*, *Vibrio mimicus*, *Vibrio hollisae*, *Vibrio fluvialis*, *Vibrio metchnikovii*, *Vibrio damsela* and *Vibrio fumisii*), *Yersinia* species (such as *Yersinia enterocolitica*, *Yersinia pestis*, and *Yersinia pseudotuberculosis*) and *Xanthomonas maltophilia* among others, wherein each possibility represents a separate embodiment of the present invention.

The term "lung disorder" or "lung disease", used herein interchangeably, refers to conditions that affect the lung, and are inclusive of lung infections that are associated with lung conditions or diseases. Such conditions include, but are not limited to, cystic fibrosis (CF), chronic obstructive pulmonary disease (COPD).

The methods of the invention both ex-vivo and in the body of the subject may further comprise co administration of at least one additional antibacterial agent such as state of the art antibiotics.

The term "antibacterial" may refer to one or more of the following effects: killing the bacteria (bacteriocide), causing halt of growth of bacteria (bacteriostatic), prevention of bacterial infection, and decrease in bacterial virulence.

The term "combating bacteria" or "treating bacterial infection" may refer to one of the following: decrease in the number of bacteria, killing or eliminating the bacteria, inhibition of bacterial growth (stasis), inhibition of bacterial infestation, decrease in bacterial virulence, or any combination thereof.

As used herein, the term "administering" refers to bringing in contact with a compound of the present invention. Administration can be accomplished to cells or tissue cultures, or to living organisms, for example humans. In one embodiment, the present invention encompasses administering the compounds of the present invention to a human subject.

A "therapeutic" treatment is a treatment administered to a subject who exhibits signs of pathology for the purpose of diminishing or eliminating those signs. A "therapeutically effective amount" is that amount of compound which is sufficient to provide a beneficial effect to the subject to which the compound is administered.

"Preventing" and "prevent" means avoiding the onset of a clinically evident disease progression altogether or slowing the onset of a pre-clinically evident stage of a disease in individuals at risk. Prevention includes prophylactic treatment of those at risk of developing a disease.

Pharmaceutical Composition:

According to an additional aspect of embodiments of the present invention, there is provided a pharmaceutical composition that includes one or more of the sphingosine analogs presented herein.

The present invention provides, in some embodiments, pharmaceutical compositions comprising, as an active ingredient, the sphingosine analogs presented herein and a pharmaceutically acceptable carrier. The term "pharmaceutically acceptable carrier" refers to a vehicle which delivers the active components to the intended target and which does not cause harm to humans or other recipient organisms. As used herein, "pharmaceutical" will be understood to encompass both human and animal pharmaceuticals. Useful carriers include, for example, water, acetone, ethanol, ethylene glycol, propylene glycol, butane-1, 3-diol, isopropyl myristate, isopropyl palmitate, or mineral oil. Use of detergents such as n-octyl-β-D-glucopyranoside (OGP) is also contemplated. Methodology and components for formulation of pharmaceutical compositions are well known, and can be found, for example, in Remington's Pharmaceutical Sciences, Eighteenth Edition, A. R. Gennaro, Ed., Mack Publishing Co. Easton Pa., 1990, the contents of which are incorporated by reference in their entirety.

Typically, pharmaceutical composition are formulated in any form appropriate to the mode of administration, for example, solutions, colloidal dispersions, emulsions (oil-in-water or water-in-oil), suspensions, creams, lotions, gels, foams, sprays, aerosol, ointment, tablets, suppositories, and the like. In some embodiments, the pharmaceutical compositions of the present invention are formulated for aerosol administration for inhalation by a subject in need thereof.

A therapeutically effective amount of the sphingosine analogs presented herein in a pharmaceutical composition, according to some embodiments of the present invention, is an amount that when administered to a subject, is capable of preventing or ameliorating an infection, e.g., bacterial infection, or one or more symptoms thereof. The effective amount of an agent or composition of the present invention administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present invention can also be administered in combination with one or more additional therapeutic compounds. Precise amounts of active ingredient required to be administered depend on the judgment of the practitioner and are peculiar to each individual.

Typically, the therapeutic agent will be administered as a pharmaceutical formulation that includes the therapeutic agent and any pharmaceutically acceptable adjuvants, carriers, excipients, and/or stabilizers, and can be in solid or liquid form, such as tablets, capsules, powders, solutions, suspensions, or emulsions. The compositions preferably contain from about 0.01 to about 99 weight percent, more preferably from about 2 to about 60 weight percent, of therapeutic agent together with the adjuvants, carriers and/or excipients. In some embodiments, an effective amount ranges from about 0.001 mg/kg to about 500 mg/kg body weight of the subject. In some embodiments, the effective amount of the agent ranges from about 0.05 mg/kg to about 30 mg/kg, from about 0.1 mg/kg to about 30 mg/kg, from about 1 mg/kg to about 25 mg/kg, 30 from about 1 mg/kg to about 20 mg/kg, or from about 1 or 2 mg/kg to about 15 mg/kg.

In some embodiments, the composition of the invention is administered by intranasal or intraoral administration, using appropriate solutions, such as nasal solutions or sprays, aerosols or inhalants. Nasal solutions are usually aqueous solutions designed to be administered to the nasal passages in drops or sprays. Typically, nasal solutions are prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal and oral preparations for inhalation, aerosols and sprays are known and include, for example, antibiotics and antihistamines and are used for asthma prophylaxis.

For intranasal or intraoral administration the composition of the invention is provided in a solution suitable for expelling the pharmaceutical dose in the form of a spray, wherein a therapeutic quantity of the pharmaceutical composition is contained within a reservoir of an apparatus for nasal or intraoral administration. The apparatus may comprise a pump spray device in which the means for expelling a dose comprises a metering pump. Alternatively, the apparatus comprises a pressurized spray device, in which the means for expelling a dose comprises a metering valve and the pharmaceutical composition further comprises a conventional propellant. Suitable propellants include one or mixture of chlorofluorocarbons, such as dichlorodifluoromethane, trichlorofluoromethane, dichloro-tetrafluoroethane, hydrofluorocarbons, such as 1,1,1,2-tetrafluoroethane (HFC-134a) and 1,1,1,2,3,3,3-heptafluoropropane (HFC-227) or carbon dioxide. Suitable pressurized spray devices are well known in the art and include those disclosed in, inter alia, WO 92/11190, U.S. Pat. Nos. 4,819,834, 4,407,481 and WO 97/09034, when adapted for producing a nasal spray, rather than an aerosol for inhalation, or a sublingual spray. The contents of the aforementioned publications are incorporated by reference herein in their entirety. Suitable nasal pump spray devices include the VP50, VP70 and VP100 models available from Valois S. A. in Marly Le Roi, France and the 50, 70 and 100 µl nasal pump sprays available from Pfeiffer GmbH in Radolfzell, Germany, although other models and sizes can be employed. In the aforementioned embodiments, a pharmaceutical dose or dose unit in accordance with the invention can be present within the metering chamber of the metering pump or valve.

Methods of treating a disease according to the invention may include administration of the pharmaceutical compositions or medicaments comprising the sphingosine analogs presented herein as a single active agent, or in combination with additional methods of treatment. In some embodiments, the one or more additional agents are selected from the group consisting of one or more ceramide reducing agents (including but not limited to ceramidase or acid ceramidase), one or more acid sphingomyelinase inhibitors, one or more agents to reduce infection, and combinations thereof. Suitable agents to reduce infection include antibiotics (e.g., inhaled Tobramycin, TOBI), reagents that block binding of pathogens to lung epithelium, reagents to reduce mucus viscosity (e.g., Dornase alfa, Pulmozyme), chaperone reagents to enhance missing protein function (e.g., Ivacaftor, Kalydeco), and combinations thereof.

The methods of treatment of the invention may be in parallel to, prior to, or following additional methods of treatment.

It is expected that during the life of a patent maturing from this application many relevant uses of the sphingosine analogs presented herein will be developed and the scope of the terms "pharmaceutical composition", "medicament" and/or "method of treatment" are intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the phrases "substantially devoid of" and/or "essentially devoid of" in the context of a certain substance, refer to a composition that is totally devoid of this substance or includes less than about 5, 1, 0.5 or 0.1 percent of the substance by total weight or volume of the composition. Alternatively, the phrases "substantially devoid of" and/or "essentially devoid of" in the context of a process, a method, a property or a characteristic, refer to a process, a composition, a structure or an article that is totally devoid of a certain process/method step, or a certain property or a certain characteristic, or a process/method wherein the certain process/method step is effected at less than about 5, 1, 0.5 or 0.1 percent compared to a given standard process/method, or property or a characteristic characterized by less than about 5, 1, 0.5 or 0.1 percent of the property or characteristic, compared to a given standard.

The term "exemplary" is used herein to mean "serving as an example, instance or illustration". Any embodiment described as "exemplary" is not necessarily to be construed as preferred or advantageous over other embodiments and/or to exclude the incorporation of features from other embodiments.

The words "optionally" or "alternatively" are used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the terms "process" and "method" refer to manners, means, techniques and procedures for accomplishing a given task including, but not limited to, those manners, means, techniques and procedures either known to, or readily developed from known manners, means, techniques and procedures by practitioners of the chemical, material, mechanical, computational and digital arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental and/or calculated support in the following examples.

EXAMPLES

Reference is now made to the following examples, which together with the above descriptions illustrate some embodiments of the invention in a non limiting fashion.

Example 1

Synthesis 2,3-Bis(((tert-butoxycarbonyl)amino)propanoic acid; To a solution of 2,3-diaminopropanoic acid, hydrochloride salt (15 g, 107 mmol) in DI water (250 ml) was added sodium bicarbonate (71.7 g, 854 mmol) portionwise. Di-tert-butyl dicarbonate (93 g, 427 mmol) in dioxane (250 ml) was added dropwise in one hour at room temperature. The resulted reaction mixture was stirred at room temperature overnight. The solution was washed with hexane (2×400 ml). The bottom aqueous phase was cooled in ice-water batch and adjusted to pH ~3 with cold 6N HCl. The product was extracted with ethyl acetate (3×500 ml). The combined ethyl acetate phase was washed with brine and dried with sodium sulfate. The product (32 g, 99% yield) was obtained as a white solid after evaporation of solvent under vacuum. TLC; single spot (chlorform:methanol 9:1, Rf 0.3). MS (negative turbo spray); m/z 303.0 (M–H$^+$), 229.1. NMR ($\delta$ ppm, CDCl3:CD3OD 8:2); 1.44 (m, 18H), 3.34 (m, 2H), 4.11 (m, 0.18H, rotatormer), 4.21 (m, 0.77H,).

General procedure for the synthesis of N-alkanyl 2,3-diaminopropanamide. 2,3-Bis(((tert-butoxycarbonyl)amino) propanoic acid (1.16 g, 3.82 mmol), N-hydroxysuccinamide (0.44 g, 3.82 mmol) and N-(3-Dimethylaminopropyl)-N'-ethylcarbodiimide hydrochloride (EDC, 1.10 g, 5.74 mmol) were dissolved in 50 ml anhydrous chloroform under nitrogen. The solution was stirred at room temperature for 2 hours. Dodecylaniline (1.00 g, 3.82 mmol) and DMAP (0.05 g, 0.38 mmol) was added. The resulted reaction mixture was stired at 50° C. under nitrogen overnight. TLC analysis showed the formation of a major product (Rf 0.6, Hexane: ethyl acetate 6:4). Solvent was removed under vacuum, the residue was dissolved in ethyl acetate (200 ml). The ethyl acetate solution was washed with DI water (200 ml), 5% citric acid (200 ml) and DI water (200). Ethyl acetate phase was dried with sodium sulfate and the solvent was evaporated under vacuum to yield a yellowish powder. The crude product was purified by silica gel column chromatography with hexane-ethyl acetate as gradient elution solvents. Di-tert-butyl (3-((4-dodecylphenyl)amino)-3-oxopropane-1,2-diyl)dicarbamate was isolated as a white powder (1.5 g, 2.74 mmol, 72% yield).

The intermediate, di-tert-butyl (3-((4-dodecylphenyl) amino)-3-oxopropane-1,2-diyl)dicarbamate, was dissolved in anhydrous dichloromethane (40 ml). The solution was cooled in ice/water bath under nitrogen. Triethylsilane (0.96 g, 8.21 mmol) and trifluoroacetic acid were added. The reaction mixture was stirred in ice/water bath for 1 hour and then warmed up to room temperature for one hour. The solvent was removed under vacuum and the residue was dissolve in chloroform (200 ml). The chloroform solution was washed with 5% aqueous sodium bicarbonate solution (200 ml) and dried with sodium sulfate. The solvent was removed under vacuum to yield an oily crude product. The crude product was purified by silica gel chromatography with chloroform/methanol/water as eluting solvents.

(R)-2,3-dianmino-N-tetradecylpropanamide; TLC; single spot (chloroform:methanol 8:2, Rf 0.5). MS (positive turbo spray); m/z 283.3, 300.0, 312.0, 326.1, 340.2, 347.9, 354.2, 368.3. NMR ($\delta$ ppm, CDCl3:CD3OD 8:2); 0.88 (m, 3H), 1.26 (m, 22H), 1.51 (m, 2H), 2.84 (m, 2H), 3.23 (m, 3H).

(S)-2,3-dianmino-N-tetradecylpropanamide; TLC; single spot (chloroform:methanol 8:2, Rf 0.5). MS (positive turbo spray); m/z 300.1, 312.0, 326, 340.3, 348.3, 354.3, 368.3. NMR ($\delta$ ppm, CDCl3:CD3OD 8:2); 0.88 (m, 3H), 1.26 (m, 22H), 1.51 (m, 2H), 2.84 (m, 2H), 3.23 (m, 3H).

(S)-2,3-dianmino-N-(4-dodecylphenyl)propanamide; TLC; single spot (chloroform:methanol 8:2, Rf 0.5). MS (positive turbo spray); m/z 331.2, 348.0, 360.0, 374.3, 388.1, 402.0, 416.3. NMR ($\delta$ ppm, CDCl3:CD3OD 8:2); 0.88 (m, 3H), 1.26 (m, 22H), 1.58 (m, 2H), 2.57 (m, 2H), 2.94 (m, 2H), 3.42 (m, 2H), 7.15 (d, 2H), 7.46 (d, 2H).

(R)-2,3-dianmino-N-(4-dodecylphenyl)propanamide; TLC; single spot (chlorform:methanol 8:2, Rf 0.5). MS (positive turbo spray); m/z 331.2, 348.0, 360.0, 374.3, 388.1, 402.0, 416.3. NMR (δ ppm, CDCl3:CD3OD 8:2); 0.88 (m, 3H), 1.26 (m, 22H), 1.58 (m, 2H), 2.57 (m, 2H), 2.94 (m, 2H), 3.42 (m, 2H), 7.15 (d, 2H), 7.46 (d, 2H).

The aforementioned methodologies were used to afford a group of sphingosine analogs, listed in Table 1 hereinbelow:

TABLE 1

| Code | Structure |
|---|---|
| 791577 | <br>(2S,3S)-2-(dimethylamino)octadecane-1,3-diol [791577] |
| 791578 | <br>(2S,3S)-1-amino-2-(dimethylamino)octadecan-3-ol [791578] |
| 791579 | <br>(2S,3R)-$N^2$,$N^2$-dimethyloctadecane-1,2,3-triamine [791579] |
| 791580 | <br>(2S,3S)-$N^2$,$N^2$-dimethyloctadecane-1,2,3-triamine [791580] |
| 791581 | <br>(E)-2-aminohexadec-5-ene-1,2-diol [791581] |
| 791582 | <br>(E)-hexadec-5-ene-1,2,2-triamine [791582] |
| 791597 | <br>(2R,3R)-1,2-diaminooctadecan-3-ol [791597] |
| 791598 | <br>(2R,3S)-octadecane-1,2,3-triamine [791598] |

TABLE 1-continued

| Code | Structure |
|---|---|
| 791601 | <br>(2R,3R,Z)-2-aminohenicos-12-ene-1,3-diol [791601] |
| 791602 | <br>(2S,3S,12Z,15Z)-2-aminohenicosa-12,15-diene-1,3-diol [791602] |
| 791993 | <br>(R)-2,3-diamino-N-tetradecylpropanamide [791993] |
| 791994 | <br>(S)-2,3-diamino-N-tetradecylpropanamide [791994] |
| 791995 | <br>(S)-2,3-diamino-N-(4-dodecylphenyl)propanamide [791995] |
| 791996 | <br>(R)-2,3-diamino-N-(4-dodecylphenyl)propanamide [791996] |
| 792205 | <br>2,3-diamino-N-(4-tetradecylphenyl)propanamide [792205] |
| 792206 | <br>(S)-2,3-diamino-N-(4-hexadecylphenyl)propanamide [792206] |

TABLE 1-continued

| Code | Structure |
|---|---|
| 792208 | 2,3-diamino-N-hexadecylpropanamide [792208] |
| 792209 | 2,3-diamino-N-octadecylpropanamide [792209] |
| 792211 | 3-amino-N-(4-dodecylphenyl)-2-hydroxypropanamide [792211] |
| 792212 | (S)-2,4-diamino-N-(4-dodecylphenyl)butanamide [792212] |

Example 2

Assays

Incubation of bacteria with the sphingosine analogs presented herein was carried out as follows. *P. aeruginosa* strain 762 was grown in LB medium at 37° C. until the early logarithmic phase ($OD_{550}$ of 0.2). Bacteria were diluted in PBS (without $Ca^{+2}$ and $Mg^{+2}$) to a concentration of $5 \times 10^3$ CFU/ml. Stock solutions of sphingolipid analogs in 5 mM in 7.5% n-octyl-β-D-glucopyranoside (OGP) or in dimethyl sulfoxide (DMSO) were prepared by sonication and warming to 40° C. The sphingosine analogs presented herein were added to the bacteria (0.05-200 µM in 0.075% OGP or 1% DMSO). Bacteria were incubated with the sphingosine analogs presented herein for 2 hours at 37° C., and 200 µl of a bacteria solution plated on LB agar plates, incubated overnight at 37° C., and colonies counted.

Ceramide synthase assays were carried out as follows. Cell homogenates were incubated with 15 µM NBD-SPH, 20 µM defatted bovine serum albumin, and 50 µM fatty acyl CoA in a 20 µl reaction volume at 37° C. Reactions were terminated by addition of chloroform/methanol (1:2, v/v) and lipids extracted. Lipids were dried under $N_2$, re-suspended in chloroform/methanol (9:1, v/v) and separated by TLC using chloroform/methanol/2M $NH_4OH$ (40:10:1, v/v/v) as the developing solvent. NBD-labelled lipids were visualized using a Typhoon 9410 variable mode imager and quantified by ImageQuantTL (GE Healthcare, Chalfont St Giles, UK).

N-acylation was determined by incubating homogenates with 15 µM dhSo, 20 µM defatted BSA and 0.01 uCi C16-[14C] acyl-CoA/46 µM C16 acyl-CoA in a final volume of 250 µl.

Example 3

Activity Assays

Figure 1A:
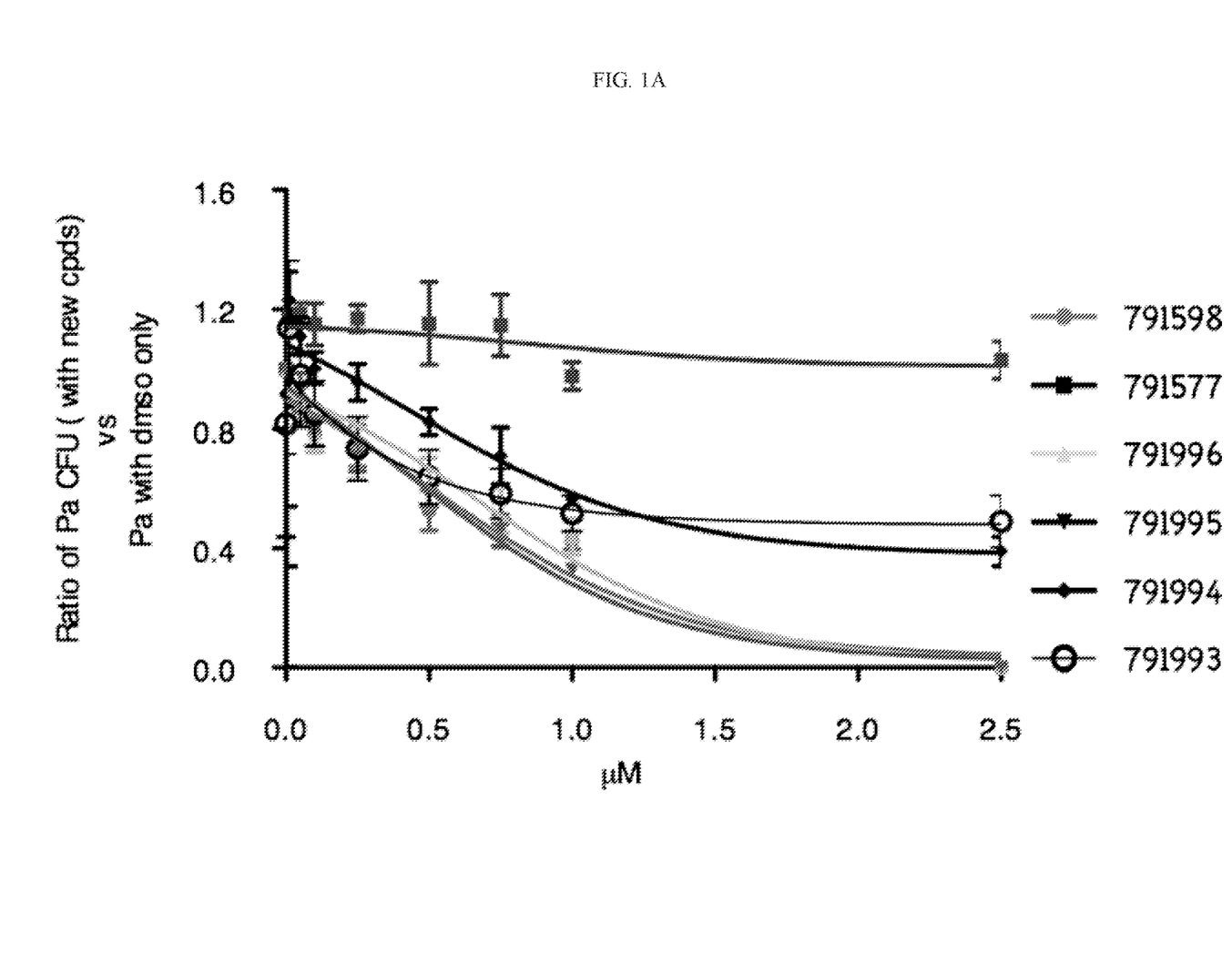
FIGS. 1A-D present comparative plots, showing the results of the *P. aeruginosa* strain 762 killing assay, consulted for the sphingosine analogs presented herein.
Figure 1B:
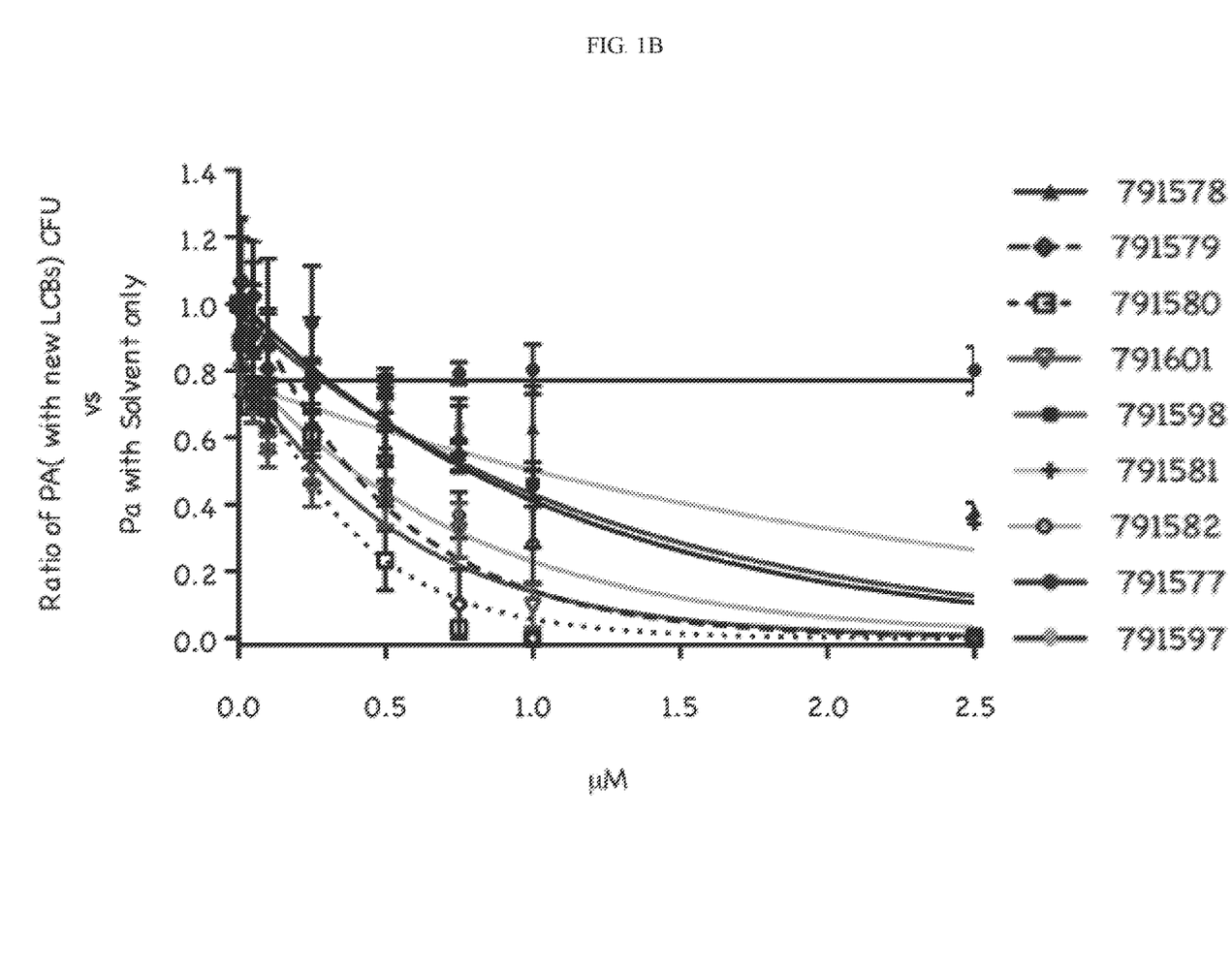
Figure 1C:
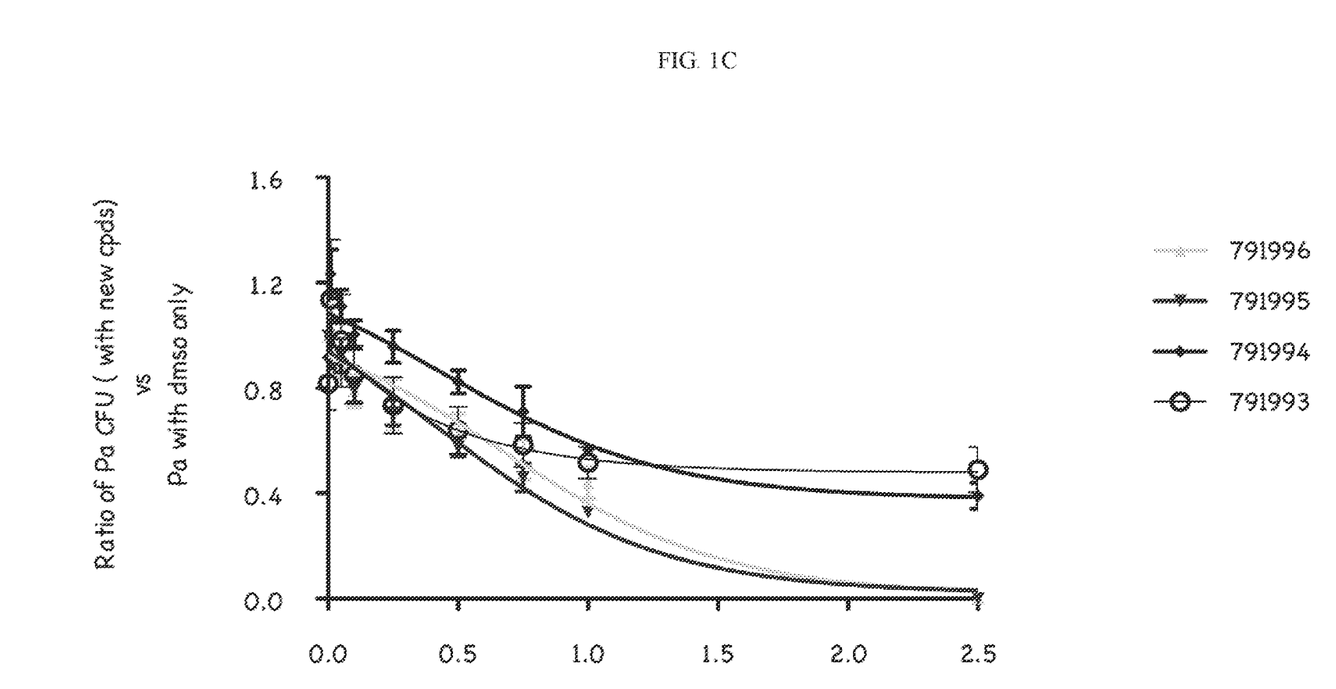
Figure 1D:
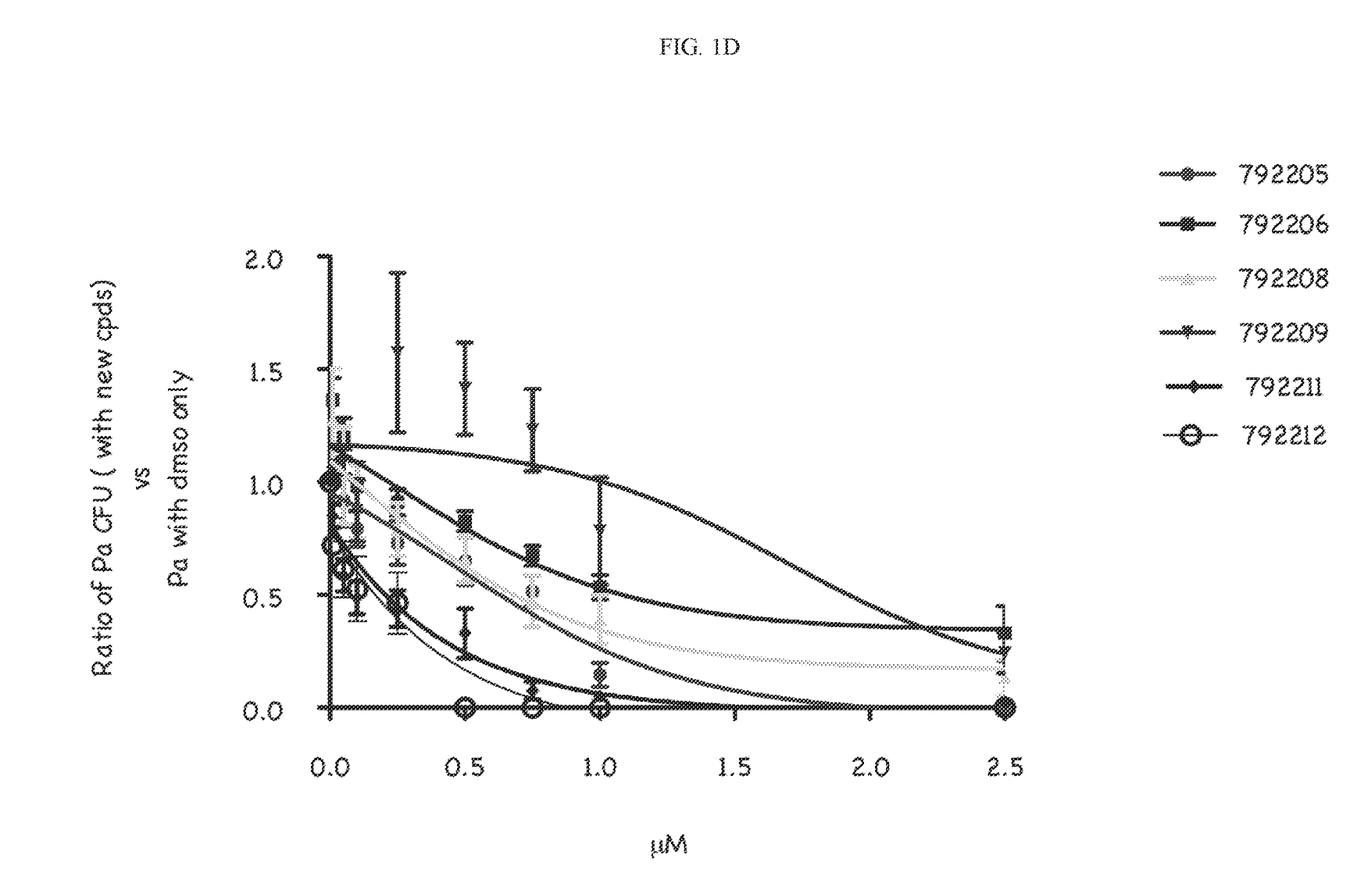

The ability of the sphingo sine analogs presented herein to kill *Pseudomonas aeruginosa* in vitro, and based on the data shown below, concluded that the SPH analogs presented herein are highly efficient in killing bacteria. Compounds 791598 and 791577 were used as activity assay control references.

FIGS. 1A-D present comparative plots, showing the results of the *P. aeruginosa* strain 762 killing assay, conducted for sphingosine analogs presented herein.

To determine whether the sphingosine analogs presented herein can be metabolized by ceramide synthases (CerS—natural sphingosine is a substrate for CerS), their N-acylation using $^{14}C$ labeled CoA as a substrate was examined. The results confirmed that neither 791995 nor 791996 could be N-acylated, demonstrating that these SPH analogs are not substrates for CerS, and indicating that there is no concern that N-acylation might be an off-target effect (raw data and results not shown).

An additional assay determined whether the sphingosine analogs presented herein are N-acylated by CerS5 expressed, relative to sphinganine (control; 100% acylation), using labeled palmitoyl CoA (n=1-2). The assay results are summarized in Table 2 below.

TABLE 2

| Compound | EC50 (μM) | N-Acylation using $^{14}C$ labeled palmitoyl CoA | Rate of N-Acylation (either pmol/mg/min or % of control) |
|---|---|---|---|
| 791577 | >2.5 | No | 4.7 ± 2.4 (0.89% of control) |
| 791578 | 1.44 ± 0.76 | No | 55.0 ± 6.0 (10.39% of control) |
| 791579 | 0.58 ± 0.14 | No | 4.1 ± 3.0 (0.77% of control) |
| 791580 | 0.39 ± 0.06 | No | 6.1 ± 2.6 (1.15% of control) |
| 791581 | 1.09 ± 0.31 | No | 4.2 ± 4.5 (0.79% of control) |
| 791582 | 0.54 ± 0.18 | No | 14.4 ± 7.7 (2.72% of control) |
| 791597 | 0.89 ± 0.23 | No | 18.8 ± 12.3 (3.55% of control) |
| 791598 | 0.99 ± 0.01 | No | 10.4 ± 10.1 (1.97% of control) |
| 791601 | 0.42 ± 0.05 | Yes | 144.6 ± 51.7 (27.32% of control) |
| 791602 | — | Yes | 146.9 ± 0.0 (27.76% of control) |
| 791993 | 0.94 ± 0.322 | — | 0.98 ± 0.09 |
| 791994 | 1.31 ± 0.4 | Yes | 25.42 ± 6.97 |
| 791995 | 0.87 ± 0.091 | No | 0.14 ± 0.004 |
| 791996 | 0.81 ± 0.24 | No | 0.02 ± 0.003 |
| 792205 | 0.61 ± 0.20 | No | 5.21 ± 1.33 |
| 792206 | 1.12 ± 0.18 | No | 3.78 ± 0.24 |
| 792208 | 0.72 ± 0.26 | — | 2.81 ± 1.06 |
| 792209 | >2.5 | No | — |
| 792211 | 0.26 ± 0.09 | Yes | 114.21 ± 3.11 |
| 792212 | 0.16 ± 0.07 | No | 2.77 ± 0.65 |

In another assay it was demonstrated that the sphingosine analogs presented herein, are not inhibitors of CerS5. The results of the assay for inhibition of ceramide synthesis measured in vitro and the results are presented in Table 3 below.

TABLE 3

| Compound | CerS5 activity (% of control) |
|---|---|
| 791580 | 58.1 ± 20.1 |
| 791601 | 88.5 ± 10.1 |
| 791582 | 68.2 ± 10.4 |
| 791579 | 69.2 ± 8.9 |
| 791597 | 125.0 ± 31.1 |
| 791598 | 111.3 ± 34.9 |
| 791581 | 71.5 ± 19.0 |
| 791578 | 90.2 ± 16.4 |
| 791577 | 92.9 ± 28.7 |
| 791602 | 57.3 ± 12.2 |
| sphinganine | 100 ± 0 |

Table 4 below presents the results for the CerS5 activity/inhibition assay using NBD sphinganine (given as percentage of control).

TABLE 4

| Compound | Concentration of compound (μM) | | | |
|---|---|---|---|---|
| | 0 | 25 | 50 | 75 |
| 791996 | 100 ± 0 | 96.67 ± 12.85 | 104.48 ± 21.24 | 105.49 ± 13.91 |
| 791995 | 100 ± 0 | 107.01 ± 24.01 | 119.01 ± 20.91 | 109.08 ± 26.94 |
| 792205 | 100 ± 0 | 98.48 ± 18.13 | 92.70 ± 19.01 | 59.41 ± 12.05 |
| 792206 | 100 ± 0 | 76.57 ± 12.85 | — | 124.85 ± 37.39 |
| 792208 | 100 ± 0 | 114.21 ± 21.36 | 81.94 ± 7.15 | 72.7 ± 5.76 |
| 792211 | 100 ± 0 | 162.86 ± 37.91 | 73.5 ± 8.98 | 49.75 ± 26.65 |
| 792212 | 100 ± 0 | 163.35 ± 82.34 | 138.24 ± 58.99 | 119.33 ± 32.79 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

What is claimed is:

1. A sphingosine analog, individually selected from the group consisting of:

(2S,3S)-1-amino-2-(dimethylamino)octadecane-3-ol [791578]

(2S,3R)-$N^2,N^2$-dimethyloctadecane-1,2,3-triamine [791579]

(2S,3S)-$N^2,N^2$-dimethyloctadecane-1,2,3-triamine [791580]

(E)-2-aminohexadec-5-ene-1,2-diol [791581]

(E)-hexadec-5-ene,1,2,2-triamine [791582]

(2R,3R)-1,2-diaminooctadecan-3-ol [791597]

(2R,3S)-octadecan-1,2,3-triamine [791598]

(2R,3R,Z)-2-aminohenicos-12-ene-1,3-diol [791601]

(2S,3S,12Z,15Z)-2-aminohenicosa-12,15-diene-1,3-diol [791602]

(R)-2,3-diamino-N-tetradecylpropanamide [791993]

(S)-2,3-diamino-N-tetradecylpropanamide [791994]

(S)-2,3-diamino-N-(4-dodecylphenyl)propanamide [791995]

(S)-2,3-diamino-N-(4-dodecylphenyl)propanamide [791996]

(S)-2,3-diamino-N-(4-dodecylphenyl)propanamide [791996]

2,3-diamino-N-(4-tetradecylphenyl)propanamide [792205]

(S)-2,3-diamino-N-(4-hexadecylphenyl)propanamide [792206]

2,3-diamino-N-hexadecylpropanamide [792208]

2,3-diamino-N-octadecylpropanamide [792209]

3-amino-N-(4-dodecylphenyl)-2-hydroxypropanamide [792211]

and (S)-2,4-diamino-N-(4-dodecylphenyl)butanamide [792212]

and any ester, solvate, hydrate and/or pharmaceutically acceptable salt thereof.

2. A pharmaceutical composition comprising as an active ingredient the sphingosine analog of claim 1.

3. The composition of claim 2, identified for use in treating a bacterial infection in a subject.

4. The composition of claim 3, wherein said bacterial infection is caused by *Pseudomonas aeruginosa*.

5. The composition of claim 3, wherein said bacterial infection is a pulmonary bacterial infection.

6. The composition of claim 3, wherein said bacterial infection is in a subject having a lung disorder or disease.

7. The composition of claim 6, wherein said lung disorder or disease is cystic fibrosis (CF).

8. A method of treating a bacterial infection in a subject in need thereof, comprising administering to the subject a therapeutically effective amount of the sphingosine analog of claim 1, wherein said infection is caused by *Pseudomonas aeruginosa*.

9. The method of claim 8, effected by inhalation.

\* \* \* \* \*